US012678387B2

(12) United States Patent
Kim et al.

(10) Patent No.: US 12,678,387 B2
(45) Date of Patent: Jul. 14, 2026

(54) COMPOSITION FOR ALLEVIATING HAIR LOSS OR PROMOTING HAIR GROWTH

(71) Applicant: LG HOUSEHOLD & HEALTH CARE LTD., Seoul (KR)

(72) Inventors: Jae-Yoon Kim, Seoul (KR); Jae-Young Shin, Seoul (KR); Yun-Ho Choi, Seoul (KR); Sang-Hwa Lee, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 786 days.

(21) Appl. No.: 17/759,310

(22) PCT Filed: Jan. 23, 2020

(86) PCT No.: PCT/KR2020/001202
§ 371 (c)(1),
(2) Date: Jul. 22, 2022

(87) PCT Pub. No.: WO2021/149853
PCT Pub. Date: Jul. 29, 2021

(65) Prior Publication Data
US 2023/0060969 A1 Mar. 2, 2023

(51) Int. Cl.
*A61K 8/60* (2006.01)
*A61K 8/9783* (2017.01)
*A61Q 7/00* (2006.01)

(52) U.S. Cl.
CPC ............ *A61K 8/602* (2013.01); *A61K 8/9783* (2017.08); *A61Q 7/00* (2013.01)

(58) Field of Classification Search
CPC .. A61K 8/602; A61K 8/9783; A61K 31/7048; A61K 31/704; A61Q 7/00; A61Q 5/00; A23L 33/125; A61P 17/14; A23V 2002/00; A23V 2200/318
See application file for complete search history.

(56) References Cited

U.S. PATENT DOCUMENTS

2004/0171693 A1* 9/2004 Gan ...................... A61K 8/606
514/565
2007/0141019 A1* 6/2007 Long ...................... A61Q 7/00
424/74

FOREIGN PATENT DOCUMENTS

| | | |
|---|---|---|
| JP | 62-93217 A | 4/1987 |
| JP | 11-12178 A | 1/1999 |
| JP | 2002-53467 A | 2/2002 |
| JP | 2009-242396 A | 10/2009 |
| JP | 2011-126914 A | 6/2011 |
| JP | 2011-522881 A | 8/2011 |
| JP | 2015-516990 A | 6/2015 |
| KR | 10-2010-0084041 A | 7/2010 |
| KR | 2010-0120545 A | 11/2010 |
| KR | 10-2063697 B1 | 1/2020 |

OTHER PUBLICATIONS

"Traditional Chinese Medicine Identification", Kang Tingguo, China Traditional Chinese Medicine Press, p. 276 (Aug. 31, 2016).
Notice of Refusal (translation) for corresponding JP Patent Appl No. 2022-544823, issued Jan. 29, 2024, 6 pages.
Kumar et al., "Formulation and Evaluation of Poly Herbal Hair Oil—An Economical Cosmetic", International Journal of Advanced Research in Medical & Pharmaceutical Sciences, vol. 1, Issue 2, 2016, pp. 10-14.
Saansoomchai et al., "Enhanced VEGF Expression in Hair Follicle Dermal Papilla Cells by Centella asiatica Linn.", CMU J. Nat. Sci., (2018), vol. 17 (1), pp. 25-37.
King et al., "Asiaticoside protects cochlear hair cells from high glucose-induced oxidative stress via suppressing AGES/RAGE/NF-KB pathway", Biomedicine & Pharmacotherapy, vol. 86, (2017), pp. 531-536.

* cited by examiner

*Primary Examiner* — Robert A Wax
*Assistant Examiner* — Quanglong N Truong
(74) *Attorney, Agent, or Firm* — Vorys, Sater, Seymour and Pease LLP; Mih Suhn Koh

(57) ABSTRACT

Provided is a composition for preventing hair loss and promoting hair growth, containing an ingredient for inducing anagen hair growth or hair growth promotion. The composition for preventing hair loss and promoting hair growth, of the presently claimed subject matter, shortens the period of telogen-to-anagen transition in the hair growth cycle, so as to promote hair growth and delay the transition to the catagen stage, thereby having the excellent effects of preventing hair loss and promoting hair growth.

3 Claims, No Drawings

COMPOSITION FOR ALLEVIATING HAIR LOSS OR PROMOTING HAIR GROWTH

TECHNICAL FIELD

The present disclosure relates to a composition for preventing hair loss and promoting hair growth, which contains an ingredient for inducing hair growth or hair growth promotion.

BACKGROUND ART

As the times change, interests in beauty are increasing day by day, in which hair is an important part. Hair is a keratinized structure produced from the skin surface. It serves as a cushion against external impact and protects the human body from external stimuli such as direct sunlight, cold, friction, etc. It is also responsible for excreting heavy metals such as arsenic, mercury, zinc, etc. out of the body and plays an important role in beauty, as the means of improving appearance. However, with the change in dietary habits or increased internal and external stresses, the number of people who suffer from hair loss due to many causes is increasing. Although genetic factors are known as the major cause of hair loss, increased social stress, environmental pollution, frequent perming and hair dyeing, wrong scalp management, etc. are also the causes of hair loss.

Human has about 100,000-150,000 hairs and each hair has a different growth cycle. The hair growth cycle consists of three stages: the anagen stage where hair grows the most actively, the catagen stage where the hair begins to degenerate, and the telogen stage where the hair growth stops or is in resting phase.

It is known that the activity of dermal papilla cells forming hair follicles and outer root sheath cells including hair follicle stem cells and various cytokines and growth factors produced by the cells play an important role in controlling the hair growth cycle. For example, Dickkopf-1 (DKK-1) plays an important role in the inhibition of growth and destruction of hair follicles (*J Invest Dermatol*, 2008: 128(2)). Meanwhile, the regeneration of hair follicles and activation of stem cells are necessary for cyclic hair growth. It is known that the regeneration and activation are achieved by the production and activation of Wnt/β-catenin (*Nature* 2007: 447 (7142)).

In general, alopecia refers to a condition of abnormally increased depilation caused by decreased proportion of hair in the anagen stage and increased proportion of hair in the catagen or telogen stage in the hair growth cycle. In the case of a normal person, the proportion of hair in the anagen stage is high, while a person suffering from alopecia has a high proportion of hair in the telogen stage and shows visible hair loss. The persons suffering from alopecia are characterized by the downsizing of hair. As alopecia proceeds, the period of the anagen stage is reduced and the transition to the catagen and telogen stages is accelerated. Then, the volume of dermal papilla is reduced and hair follicles are downsized gradually. Therefore, in order to treat alopecia, it is important to recover hair in the telogen phase rapidly to the anagen phase and to extend the anagen stage.

Male-pattern hair loss, which is the alopecia with the most patients, is also called 'androgenic alopecia'. Male-pattern hair loss occurs primarily in young men in their twenties to thirties. It is because androgenic alopecia is affected not only by genetic factors but also by the action of male hormone and age. The male hormone testosterone is known as the major cause of male-pattern hair loss, and the male-pattern hair loss is classified variously depending on the shape and progress of bald patches. Testosterone-induced male-pattern hair loss occurs as dihydrotestosterone (DHT) produced from the male hormone by the enzyme 5α-reductase acts on hair follicles to inhibit cell division and hair growth.

The type of hair loss changes depending on the distribution of the enzyme 5α-reductase on the scalp. Hair thinning and loss occur at the crown of the scalp where the enzyme is distributed a lot because cell division is decreased and the hair cycle is shortened due to DHT. In contrast, at the temporal or occipital part, hair loss does not occur easily because of relatively weak activity of the enzyme and the effect of female hormone. At present, hair transplantation, medication, etc. are used for management of male-pattern hair loss.

Although excessive action of male hormones, excessive sebum secretion, poor blood circulation, deterioration of scalp function due to peroxides, bacteria, etc., genetic factors, aging, stress, etc. have been discussed as the cause of hair loss, the cause of hair loss has not been clearly elucidated yet. Although currently available products for preventing hair loss contain ingredients for promoting blood circulation, enhancing hair root function, moisturizing the scalp, preventing dandruffs, preventing oxidation, extending the anagen phase, inhibiting the action of male hormones, etc. as active ingredients, they do not provide distinct effects and have side effects.

The medications for treating or preventing alopecia developed thus far include drugs containing female hormones as active ingredients, for promoting blood circulation, enhancing hair root function, moisturizing the scalp and inhibiting male hormones and drugs including minoxidil, finasteride, trichosaccharide. Minoxidil (2,4-diamino-6-piperidinopyrimidine 3-oxide), which is the representative topical medication for hair loss, increases blood flow to the scalp. And, finasteride, which is an oral medication used to treat hair loss, decreases the production of the active male hormone DHT by inhibiting the activity of 5α-reductase. However, these medications have many limitations due to side effects or cautions to be observed during use.

DISCLOSURE

Technical Problem

The present disclosure is directed to providing a composition for preventing hair loss or promoting hair growth, which has superior effect of preventing hair loss or promoting hair growth while being safe for the human body with no side effect.

The present disclosure is also directed to providing a product for hair or scalp, which contains the composition for preventing hair loss or promoting hair growth.

Technical Solution

The inventors of the present disclosure have made consistent efforts to develop a composition that can effectively promote hair growth while being safe for the human body without the problems of the side effects and cautions to be observed during use of the existing medications for treating hair loss. As a result, they have found out that a composition containing momordin Ic, platycodin D2, polygalacin D, asiaticoside B, bacopaside I, notoginsenoside R2, picfeltarraenin IB, pseudoginsenoside RT5, raddeanin A, vina-ginsenoside R4 or ziyuglycoside II as an active ingredient has a remarkably superior effect of preventing hair loss and promoting hair growth, and have completed the present disclosure.

Specifically, the inventors of the present disclosure have identified that each of the active ingredients described above enhances the activity of dermal papilla cells, promotes the activity of mitochondria in dermal papilla cells, promotes the activity of the Wnt/β-catenin signaling pathway and inhibits the action of male hormones. That is to say, it has been identified through in-vitro experiments that each of the active ingredients described above plays an important role in transiting the hair growth cycle from the catagen phase to the growth phase by enhancing the activity of dermal papilla cells and amplifying the Wnt/β-catenin signaling. In addition, the inventors of the present disclosure have identified that the treatment of a composition for treating hair loss, containing the active ingredients, to patient with alopecia provides a remarkably superior effect of improving hair density and thickness. Furthermore, as a result of comparative experiment with the commercially available minoxidil, it has been identified that the composition for treating hair loss, containing the active ingredients, to patient with alopecia provides a remarkably superior effect of preventing hair loss and promoting hair growth as compared to minoxidil.

The present disclosure provides a composition for preventing hair loss or promoting hair growth, which contains one or more selected from a group consisting of momordin Ic, platycodin D2, polygalacin D, asiaticoside B, bacopaside I, notoginsenoside R2, picfeltarraenin IB, pseudoginsenoside RT5, raddeanin A, vina-ginsenoside R4 and ziyuglycoside II as an active ingredient.

In an exemplary embodiment, the eleven active ingredients may be derived from plants. The momordin Ic is an ingredient derived from kochiae fructus, the platycodin D2 is an ingredient derived from balloon flower (*Platycodon grandiflorum* (Jacq.) A.DC.), the polygalacin D is an ingredient derived from polygalae radix, the asiaticoside B is an ingredient derived from gotu kola (*Centella asiatica* (L.) Urb.), the bacopaside I is an ingredient derived from water hyssop (*Bacopa monnieri* (L.) Wettst.), the notoginsenoside R2 is an ingredient derived from Chinese ginseng (*Panax notoginseng*), the picfeltarraenin IB is an ingredient derived from Chinese figwort (*Scrophularia ningpoensis* Hemsl.), the pseudoginsenoside RT5 and vina-ginsenoside R4 are ingredients derived from ginseng (ginseng radix et rhizoma), the raddeanin A is an ingredient derived from *Anemone raddeana* Regel, and the ziyuglycoside II is an ingredient derived from sanguisorbae radix.

In an exemplary embodiment, the momordin Ic may be contained in an amount of 0.00001-50 wt %, specifically 0.0001-0.1 wt %, based on the total weight of the composition. The platycodin D2 may be contained in an amount of 0.00001-50 wt %, specifically 0.0001-0.1 wt %, based on the total weight of the composition. The polygalacin D may be contained in an amount of 0.00001-50 wt %, specifically 0.0001-0.1 wt %, based on the total weight of the composition. The asiaticoside B may be contained in an amount of 0.00001-50 wt %, specifically 0.0001-0.1 wt %, based on the total weight of the composition. The bacopaside I may be contained in an amount of 0.00001-50 wt %, specifically 0.0001-0.1 wt %, based on the total weight of the composition. The notoginsenoside R2 may be contained in an amount of 0.00001-50 wt %, specifically 0.0001-0.1 wt %, based on the total weight of the composition. The picfeltarraenin IB may be contained in an amount of 0.00001-50 wt %, specifically 0.0001-0.1 wt %, based on the total weight of the composition. The pseudoginsenoside RT5 may be contained in an amount of 0.00001-50 wt %, specifically 0.0001-0.1 wt %, based on the total weight of the composition. The raddeanin A may be contained in an amount of 0.00001-50 wt %, specifically 0.0001-0.1 wt %, based on the total weight of the composition. The vina-ginsenoside R4 may be contained in an amount of 0.00001-50 wt %, specifically 0.0001-0.1 wt %, based on the total weight of the composition. The ziyuglycoside II may be contained in an amount of 0.00001-50 wt %, specifically 0.0001-0.1 wt %, based on the total weight of the composition.

When the content of each active ingredient is 0.00001-50 wt %, specifically 0.0001-0.1 wt %, based on the total weight of the composition, superior effect of preventing hair loss and promoting hair growth is achieved in in-vitro experiments or clinically. When the content of the active ingredient is less than 0.0001 wt % based on the total weight of the composition, the effect of promoting hair growth is insignificant. And, when it exceeds 50 wt %, formulation stability is unsatisfactory.

The present disclosure also provides a pharmaceutical composition, a quasi-drug composition, a cosmetic composition or a functional health food composition, which contains the composition for preventing hair loss or promoting hair growth. The composition of the present disclosure may be prepared into any formulation that can be commonly applied to skin. Specifically, it may be prepared into a formulation for external application to skin. The composition of the present disclosure may be prepared into a formulation that can be applied to skin, for example, a liquid, a cream, a paste, a solid, etc.

The one or more selected from a group consisting of momordin Ic, platycodin D2, polygalacin D, asiaticoside B, bacopaside I, notoginsenoside R2, picfeltarraenin IB, pseudoginsenoside RT5, raddeanin A, vina-ginsenoside R4 and ziyuglycoside II of the present disclosure may be contained in the composition or formulation as an agent for preventing hair loss or an agent for promoting hair growth.

In an exemplary embodiment, when the formulation of the present disclosure is a liquid, a solvent, a solubilizer, an emulsifier, etc. may be used as a carrier ingredient. For example, water, an alcohol, ethyl carbonate, ethyl acetate, benzyl alcohol, benzyl benzoate, propylene glycol, 1,3-butylene glycol, glycerol, an aliphatic ester, polyethylene glycol, a fatty acid ester of sorbitan, etc. may be used. The alcohol may be specifically a linear or branched $C_2$-$C_4$ monoalcohol, more specifically ethanol or isopropanol. Particularly, the transdermal absorption of the composition for preventing hair loss or promoting hair growth may be facilitated when ethanol or isopropanol is used as the carrier ingredient.

In an exemplary embodiment, when the formulation of the present disclosure is a paste, a cream or a gel, an alcohol, an animal oil, a plant oil, a wax, paraffin, starch, tragacanth, a cellulose derivative, polyethylene glycol, silicone, bentonite, silica, talc, zinc oxide, etc. may be used as a carrier ingredient. Specifically, an alcohol may be used. More specifically, the alcohol may be isopropanol.

In an exemplary embodiment, when the formulation of the present disclosure is a powder or a spray, lactose, talc, silica, aluminum hydroxide, calcium silicate, polyamide powder, etc. may be used as a carrier ingredient. Particularly, a spray formulation may further contain a propellant such as chlorofluorohydrocarbon, propane/butane, dimethyl ether, etc.

In an exemplary embodiment, the composition of the present disclosure may further contain, in addition to momordin Ic, platycodin D2, polygalacin D, asiaticoside B, bacopaside I, notoginsenoside R2, picfeltarraenin IB, pseudoginsenoside RT5, raddeanin A, vina-ginsenoside R4 and ziyuglycoside II, ingredients commonly used in formulations for external application to skin. For example, it may further contain one or more additive selected from a group consisting of water, a surfactant, a wetting agent, an alcohol, a chelating agent, a sterilizer, an antioxidant, an antiseptic, a colorant, a flavorant, etc.

The present disclosure also provides a product for hair or scalp, which contains the composition for preventing hair loss or promoting hair growth. The product for hair or scalp may be one selected from a group consisting of a hair restorer, a scalp clinic agent, a scalp scaling agent, a scalp massage agent, a scalp care agent, a cleanser, a shampoo, a tonic, a hair conditioner, a hair lotion, a gel, a pack, a cream, an essence, a powder, a spray, an oil, a soap, an ointment, a hair styling agent, a hair dye, a hair perm agent, etc., although not being limited thereto.

In an exemplary embodiment, the composition of the present disclosure for preventing hair loss or promoting hair growth may be prepared into a formulation of a hair tonic or a hair lotion. Specifically, the composition of the present disclosure for promoting hair growth may be used through transdermal administration, e.g., by directly applying or spraying onto skin.

The present disclosure also provides a functional health food composition containing the composition for preventing hair loss or promoting hair growth. The functional health food may be prepared by a method commonly used in the art, and ingredients and components commonly used in the art may be added during the preparation. The formulation of the functional health food is not limited and any formulation acknowledged as long as it is acknowledged as a functional health food. The functional health food of the present disclosure may be prepared into various formulations. Unlike general drugs, it is advantageous in that it has no side effect, etc. that may occur during long-term intake because it is prepared from food ingredients and has superior portability. Therefore, the functional health food of the present disclosure may be used as an adjuvant for enhancing the effect of preventing hair loss and promoting hair growth.

The present disclosure also provides a method for preventing(alleviating) hair loss or promoting hair growth, which includes a step of administering a composition for preventing hair loss or promoting hair growth, which comprises one or more selected from a group consisting of momordin Ic, platycodin D2, polygalacin D, asiaticoside B, bacopaside I, notoginsenoside R2, picfeltarraenin IB, pseudoginsenoside RT5, raddeanin A, vina-ginsenoside R4 and ziyuglycoside II as an active ingredient, to a patient (subject).

The term "administration" used in the present disclosure may mean introduction of the composition of the present disclosure by any appropriate method. The composition of the present disclosure may be administered through any general administration route by which the composition can be delivered to a target tissue. The composition of the present disclosure may be administered transdermally or dermally, specifically transdermally, most specifically by topical application. The number of application of the composition of the present disclosure may be determined depending on prescription, necessity or purpose.

The administration amount of the composition of the present disclosure may be adjusted adequately depending on the induvial difference in age, legions, etc. or formulation. Specifically, an appropriate amount may be applied to the scalp for 1 week to several months, once or several times a day. In a test example of the present disclosure, the composition for treating hair loss 1 was used for 6 months, 5 times a week, and a superior effect of promoting hair growth was achieved (Test Example 5).

Advantageous Effects

The composition for preventing hair loss and promoting hair growth of the present disclosure exhibits superior effect of preventing hair loss and promoting hair growth by reducing the period of telogen-to-anagen transition in the hair growth cycle and delaying transition to the catagen phase.

BEST MODE

Hereinafter, the present disclosure is described in more detail through examples, etc. However, the examples of the present disclosure may be changed into various forms and it should not be construed that the scope of the present disclosure is not limited by the following examples. The examples of the present disclosure are provided so that the present disclosure is more completely understood by those having ordinary knowledge in the art.

Preparation of Composition for Treating Hair Loss (Hair Tonic)

Hair tonic compositions of Examples 1 to 11-2, which contain momordin Ic, platycodin D2, polygalacin D, asiaticoside B, bacopaside I, notoginsenoside R2, picfeltarraenin IB, pseudoginsenoside RT5, raddeanin A, vina-ginsenoside R4 or ziyuglycoside II as an active ingredient, were prepared as described in Table 1.

The substances and reagents used in the examples of the present disclosure were purchased from cosmetic material manufactures and commercial vendors.

TABLE 1

| Ingredients | | Ethanol | Castor oil | Glycerin | Active ingredient | | Flavorant and colorant | Purified water |
|---|---|---|---|---|---|---|---|---|
| Weight ratio (%) | Comp. Ex. 1 | 55 | 5 | 3 | — | | Adequate | Balance (100 in total) |
| | Comp. Ex. 2 | 55 | 5 | 3 | Minoxidil | 2 μg/mL | Adequate | |
| | Comp. Ex. 3 | 0 | 5 | 3 | — | | Adequate | |
| | Ex. 1 | 55 | 5 | 3 | Momordin Ic | 100 μg/mL | Adequate | |
| | Ex. 1-2 | 0 | 5 | 3 | Momordin Ic | 100 μg/mL | Adequate | |
| | Ex. 2 | 55 | 5 | 3 | Platycodin D2 | 100 μg/mL | Adequate | |
| | Ex. 2-2 | 0 | 5 | 3 | Platycodin D2 | 100 μg/mL | Adequate | |

TABLE 1-continued

| Ingredients | Ethanol | Castor oil | Glycerin | Active ingredient | | Flavorant and colorant | Purified water |
|---|---|---|---|---|---|---|---|
| Ex. 3 | 55 | 5 | 3 | Polygalacin D | 100 μg/mL | Adequate | |
| Ex. 3-2 | 0 | 5 | 3 | Polygalacin D | 100 μg/mL | Adequate | |
| Ex. 4 | 55 | 5 | 3 | Asiaticoside B | 100 μg/mL | Adequate | |
| Ex. 4-2 | 0 | 5 | 3 | Asiaticoside B | 100 μg/mL | Adequate | |
| Ex. 5 | 55 | 5 | 3 | Bacopaside 1 | 100 μg/mL | Adequate | |
| Ex. 5-2 | 0 | 5 | 3 | Bacopaside 1 | 100 μg/mL | Adequate | |
| Ex. 6 | 55 | 5 | 3 | Notoginsenoside R2 | 100 μg/mL | Adequate | |
| Ex. 6-2 | 0 | 5 | 3 | Notoginsenoside R2 | 100 μg/mL | Adequate | |
| Ex. 7 | 55 | 5 | 3 | Picfeltarraenin IB | 100 μg/mL | Adequate | |
| Ex. 7-2 | 0 | 5 | 3 | Picfeltarraenin IB | 100 μg/mL | Adequate | |
| Ex. 8 | 55 | 5 | 3 | Pseudoginsenoside RT5 | 100 μg/mL | Adequate | |
| Ex. 8-2 | 0 | 5 | 3 | Pseudoginsenoside RT5 | 100 μg/mL | Adequate | |
| Ex. 9 | 55 | 5 | 3 | Raddeanin A | 100 μg/mL | Adequate | |
| Ex. 9-2 | 0 | 5 | 3 | Raddeanin A | 100 μg/mL | Adequate | |
| Ex. 10 | 55 | 5 | 3 | Vina-ginsenoside R4 | 100 μg/mL | Adequate | |
| Ex. 10-2 | 0 | 5 | 3 | Vina-ginsenoside R4 | 100 μg/mL | Adequate | |
| Ex. 11 | 55 | 5 | 3 | Ziyuglycoside II | 100 μg/mL | Adequate | |
| Ex. 11-2 | 0 | 5 | 3 | Ziyuglycoside II | 100 μg/mL | Adequate | |

Preparation of Composition for Treating Hair Loss (Hair Lotion)

Hair lotion compositions, which contain momordin Ic, platycodin D2, polygalacin D, asiaticoside B, bacopaside I, notoginsenoside R2, picfeltarraenin IB, pseudoginsenoside RT5, raddeanin A, vina-ginsenoside R4 or ziyuglycoside II as an active ingredient, were prepared as described in Table 2.

TABLE 2

| Ingredients | Weight ratio (%) |
|---|---|
| Cetostearyl alcohol | 2 |
| Stearyl triethyl ammonium chloride | 2 |
| Hydroxyethyl cellulose | 0.5 |
| Momordin Ic, platycodin D2, polygalacin D, asiaticoside B, bacopaside I, notoginsenoside R2, picfeltarraenin IB, pseudoginsenoside RT5, raddeanin A, vina-ginsenoside R4 or ziyuglycoside II | 0.01 |
| Flavorant and colorant | Adequate |
| Purified water | Balance (100 in total) |

TEST EXAMPLE 1

Enhancement of Activity of Dermal Papilla Cells

Human-derived dermal papilla cells (DPCs) were purchased from PromoCell. The DPCs were cultured in DMEM (Hyclone Inc., UT, USA) containing 5% fetal bovine serum (FBS; GIBCO, NY, USA), 100 units/mL penicillin and 100 μg/mL streptomycin under the condition of 37° C. and 5% $CO_2$. The cultured DPCs were seeded onto a 96-well plate at 3,000 cells/well and then cultured for 24 hours under a 0.1% serum condition. Then, the cultured cells were treated and incubated for a day with serum-free DMEM diluted with DMSO (vehicle) to 1:1000 as a control group, 2 μg/mL minoxidil as a positive control group, or each of momordin Ic, platycodin D2, polygalacin D, asiaticoside B, bacopaside I, notoginsenoside R2, picfeltarraenin IB, pseudoginsenoside RT5, raddeanin A, vina-ginsenoside R4 and ziyuglycoside II, as described in Table 3. After the incubation, the enhancement of cellular activity was evaluated by the CCK method. The cell culture was treated and incubated with CCK-8 at 1:10 for 1 hour. 1 hour later, the absorbance of each well was measured at 450 nm. All the experiments were 3 times and the absorbance was averaged. The result was expressed as percentage of the control group as 100.

TABLE 3

| Groups | Concen-tration | Activity of dermal papilla cells (%) |
|---|---|---|
| Untreated | — | 100% |
| Minoxidil | 2 μg/mL | 121% |
| Momordin Ic | 10 μg/mL | 148% |
| Platycodin D2 | 10 μg/mL | 162% |
| Polygalacin D | 10 μg/mL | 164% |
| Asiaticoside B | 10 μg/mL | 131% |
| Bacopaside I | 10 μg/mL | 133% |
| Notoginsenoside R2 | 10 μg/mL | 131% |
| Picfeltarraenin IB | 10 μg/mL | 139% |
| Pseudoginsenoside RT5 | 10 μg/mL | 141% |
| Raddeanin A | 10 μg/mL | 130% |
| Vina-ginsenoside R4 | 10 μg/mL | 137% |
| Ziyuglycoside II | 10 μg/mL | 139% |

As a result, it was confirmed that the treatment with momordin Ic, platycodin D2, polygalacin D, asiaticoside B, bacopaside I, notoginsenoside R2, picfeltarraenin IB, pseudoginsenoside RT5, raddeanin A, vina-ginsenoside R4 or ziyuglycoside II has superior effect of enhancing the activity of dermal papilla cells and promoting the proliferation of the DPCs.

TEST EXAMPLE 2

Enhancement of Mitochondrial Activity of Dermal Papilla Cells

Human-derived dermal papilla cells (DPCs) were purchased from PromoCell. The DPCs were cultured in DMEM (Hyclone Inc., UT, USA) containing 5% fetal bovine serum (FBS; GIBCO, NY, USA), 100 units/mL penicillin and 100 μg/mL streptomycin under the condition of 37° C. and 5% $CO_2$. The cultured DPCs were seeded onto a 96-well plate at 3,000 cells/well and then cultured for 24 hours under a 0.1% serum condition. Then, the cultured cells were treated and incubated for a day with serum-free DMEM diluted with DMSO (vehicle) to 1:1000 as a control group, 2 μg/mL minoxidil as a positive control group, or each of momordin Ic, platycodin D2, polygalacin D, asiaticoside B, bacopaside I, notoginsenoside R2, picfeltarraenin IB, pseudoginsenoside RT5, raddeanin A, vina-ginsenoside R4 and ziyuglycoside II, as described in Table 4. After the incubation, the degree of cell proliferation was evaluated by the JC-1 method. The cell culture was treated and incubated with JC-1 at 1:100 for 1 hour. 1 hour later, the fluorescence of each well was measured at 590 nm and 530 nm. All the experiments were 3 times and the fluorescence intensity was averaged. The result was expressed as percentage of the control group as 100.

TABLE 4

| Groups | Concen- tration | Mitochondrial activity of dermal papilla cells (%) |
|---|---|---|
| Untreated group | — | 100% |
| Minoxidil | 2 μg/mL | 129% |
| Momordin Ic | 10 μg/mL | 120% |
| Asiaticoside B | 10 μg/mL | 151% |
| Bacopaside I | 10 μg/mL | 110% |
| Notoginsenoside R2 | 10 μg/mL | 117% |
| Pseudoginsenoside RT5 | 10 μg/mL | 112% |
| Vina-ginsenoside R4 | 10 μg/mL | 111% |
| Ziyuglycoside II | 10 μg/mL | 105% |

As a result, the treatment with momordin Ic, asiaticoside B, bacopaside I, notoginsenoside R2, pseudoginsenoside RT5, vina-ginsenoside R4 or ziyuglycoside II resulted in a superior effect of enhancing the mitochondrial activity of the dermal papilla cells.

TEST EXAMPLE 3

Regulation of Wnt/β-Catenin Signaling in Dermal Papilla Cells

In general, the Wnt/β-catenin signaling activated in the dermal papillae during transition from the catagen to the anagen transition in the hair growth cycle begins as the hair starts to grow and occurs throughout the anagen phase. In the telogen and catagen phases, the Wnt/β-catenin signaling decreases or disappears, resulting in degeneration of hair follicles and shedding of hair. Therefore, it was investigated in the examples how much the momordin Ic, platycodin D2, polygalacin D or pseudoginsenoside RT5 of the present disclosure contributes to the amplification of Wnt/β-catenin signaling.

Wnt3a protein was used as a positive control group for amplifying Wnt/β-catenin signaling, and DMSO was used as a negative control group. After seeding Wnt Reporter HEK293A cells in a 96-well culture plate, with $3\times10^4$ cells per well, and then treating with the momordin Ic, platycodin D2, polygalacin D or pseudoginsenoside RT5 of the present disclosure as described in Table 5, reporter assay was conducted using a Promega's luciferase assay kit (E1960). The experiment was conducted according to the manufacturer's instructions and the activity of the Wnt/β-catenin promoter was measured using a luminometer (Victor; Perki-nElmer, Waltham, Massachusetts, USA).

TABLE 5

| Groups | Concen- tration | Wnt signaling activity for activating hair follicles (%) |
|---|---|---|
| Untreated group | — | 100% |
| Minoxidil | 2 μg/mL | 82% |
| Momordin Ic | 10 μg/mL | 370% |
| Platycodin D2 | 10 μg/mL | 216% |
| Polygalacin D | 10 μg/mL | 293% |
| Pseudoginsenoside RT5 | 10 μg/mL | 120% |

As a result, the treatment with momordin Ic, platycodin D2, polygalacin D or pseudoginsenoside RT5 resulted in superior Wnt signaling activity. Accordingly, it was confirmed that the momordin Ic, platycodin D2, polygalacin D or pseudoginsenoside RT5 enhances the activity of the Wnt/β-catenin signaling pathway, which facilitates hair growth by hair follicle stem cells, very superiorly and, therefore, is effective in promoting hair growth.

TEST EXAMPLE 4

Androgenic Activity

A stable cell line constructed by permanently transfecting androgen receptor-positive 22Rv1 human prostate cancer cells with the pGL4.36-MMTV-Luc vector, which possesses two androgen-responsive elements and a firefly luciferase reporter gene, was used for this experiment. The stable cell line was maintained by subculturing using RPMI1640 and 10% fetal bovine serum (GIBCO BRL, Gaithersburg, MD, USA). For transcriptional activation assay, the cells were seeded in a 96-well plate, with 25,000 cells per well, while replacing the medium with phenol red-free RPMI1640 containing 5% charcoal-stripped fetal bovine serum. After culturing in an incubator at 37° C. for 48 hours and then treating with momordin Ic, platycodin D2, polygalacin D, asiaticoside B, bacopaside I, notoginsenoside R2, pseudoginsenoside RT5, raddeanin A or vina-ginsenoside R4 together with 1 nM DHT as described in Table 6, the cells were cultured for 24 hours and the inhibition of luciferase activity increased by DHT was measured using a luciferase assay system (Promega). The result was expressed as the inhibition of the luciferase activity by momordin Ic, platycodin D2, polygalacin D, asiaticoside B, bacopaside I, notoginsenoside R2, pseudoginsenoside RT5, raddeanin A or vina-ginsenoside R4 with respect to the luciferase activity increased by treatment with 1 M DHT as 100%. Bicalutamide (Casodex) was used as a positive control group and CCK-8 assay was conducted in parallel to investigate cytotoxicity. The cell culture was treated and incubated with CCK-8 at 1:10 for 2 hours. 2 hour later, the absorbance of each well was measured at 450 nm. All the experiments were 3 times and the absorbance was averaged. The result was expressed as percentage of the group treated with 1 nM DHT as 100%.

TABLE 6

| Groups | Concentration | Inhibition of androgenic activity (%) |
|---|---|---|
| Untreated group | — | 0% |
| Bicalutamide | 20 μM | 85% |
| Minoxidil | 2 μg/mL | 0% |
| Momordin Ic | 10 μg/mL | 12% |
| Platycodin D2 | 10 μg/mL | 16% |
| Polygalacin D | 10 μg/mL | 26% |
| Asiaticoside B | 10 μg/mL | 6% |
| Bacopaside I | 10 μg/mL | 6% |
| Notoginsenoside R2 | 10 μg/mL | 29% |
| Pseudoginsenoside RT5 | 10 μg/mL | 8% |
| Raddeanin A | 10 μg/mL | 10% |
| Vina-ginsenoside R4 | 10 μg/mL | 4% |

As a result, the treatment with platycodin D2, polygalacin D or notoginsenoside R2 resulted in superior effect of inhibiting androgenic activity.

TEST EXAMPLE 5

Hair-Growing Effect of Composition for Treating Hair Loss and Promoting Hair Growth Composition (Hair Tonic)

The hair-growing effect of the composition for treating hair loss and promoting hair growth of the present disclosure (hair tonic) was tested for a total of 190 males and females who have significantly fewer hairs than normal people or have the symptoms of hair loss. Different compositions were applied on the left and right parts of the scalp of the 190 males and females. The compositions of Comparative Examples 1, 2 and 3 and Examples 1 to 11-2 were applied to the hair and scalp for 6 months, 5 times a week, to 25 groups of 15 people. Then, evaluation was carried out using clinical images and a phototrichogram. The evaluation using clinical images was conducted 2 months and 6 months after the application on a 3-point scale ('good', 'slight' and 'no change'; good: 50-75% improved, slight: 25-50% improved, no change: not improved). The evaluation using a photototrichogram was conducted 6 months after the application by measuring the number of hairs per unit area and average hair thickness for Comparative Examples and Examples. The result is shown in Table 7.

TABLE 7

| | Evaluation using clinical images | | | | | | Phototrichogram | | | |
|---|---|---|---|---|---|---|---|---|---|---|
| | No change (No.) | | Slight (No.) | | Good (No.) | | Number of hairs per unit area (hairs/cm$^2$) | | Average hair thickness (μm) | |
| | 2 months | 6 months | 2 months | 6 months | 2 months | 6 months | 0 month | 6 months | 0 month | 6 months |
| Comp. Ex. 1 | 14 | 12 | 1 | 1 | 0 | 2 | 103 ± 21 | 109 ± 22 | 55 ± 2 | 58 ± 1 |
| Comp. Ex. 2 | 9 | 2 | 5 | 4 | 1 | 9 | 105 ± 23 | 168 ± 21 | 62 ± 4 | 70 ± 2 |
| Comp. Ex. 3 | 13 | 13 | 2 | 1 | 0 | 1 | 98 ± 12 | 102 ± 19 | 52 ± 4 | 55 ± 6 |
| Ex. 1 | 9 | 3 | 5 | 2 | 1 | 10 | 100 ± 19 | 219 ± 23 | 59 ± 3 | 80 ± 2 |
| Ex. 1-2 | 10 | 5 | 3 | 4 | 2 | 6 | 101 ± 21 | 150 ± 28 | 53 ± 2 | 70 ± 6 |
| Ex. 2 | 8 | 3 | 4 | 3 | 3 | 9 | 102 ± 20 | 224 ± 19 | 56 ± 6 | 83 ± 3 |
| Ex. 2-2 | 11 | 6 | 2 | 5 | 2 | 4 | 100 ± 23 | 162 ± 17 | 51 ± 2 | 68 ± 5 |
| Ex. 3 | 9 | 4 | 3 | 6 | 3 | 5 | 112 ± 22 | 180 ± 28 | 55 ± 3 | 79 ± 3 |
| Ex. 3-2 | 10 | 8 | 2 | 5 | 3 | 2 | 103 ± 18 | 141 ± 13 | 51 ± 1 | 72 ± 5 |
| Ex. 4 | 9 | 2 | 2 | 4 | 4 | 9 | 109 ± 23 | 192 ± 23 | 54 ± 2 | 76 ± 6 |
| Ex. 4-2 | 12 | 4 | 3 | 6 | 0 | 5 | 100 ± 20 | 157 ± 19 | 54 ± 5 | 64 ± 4 |
| Ex. 5 | 9 | 2 | 2 | 5 | 4 | 8 | 108 ± 23 | 178 ± 28 | 55 ± 3 | 72 ± 4 |
| Ex. 5-2 | 11 | 3 | 3 | 7 | 1 | 5 | 105 ± 23 | 150 ± 24 | 50 ± 4 | 73 ± 4 |
| Ex. 6 | 8 | 4 | 3 | 6 | 4 | 5 | 101 ± 20 | 171 ± 18 | 51 ± 2 | 75 ± 2 |
| Ex. 6-2 | 10 | 7 | 4 | 6 | 1 | 2 | 107 ± 22 | 168 ± 26 | 57 ± 4 | 69 ± 3 |
| Ex. 7 | 10 | 3 | 4 | 8 | 1 | 4 | 105 ± 25 | 158 ± 23 | 52 ± 7 | 70 ± 2 |
| Ex. 7-2 | 13 | 5 | 2 | 7 | 0 | 3 | 102 ± 25 | 142 ± 18 | 52 ± 3 | 65 ± 5 |
| Ex. 8 | 11 | 2 | 3 | 6 | 1 | 7 | 106 ± 28 | 181 ± 25 | 59 ± 8 | 80 ± 8 |
| Ex. 8-2 | 12 | 4 | 2 | 7 | 1 | 4 | 106 ± 15 | 161 ± 30 | 50 ± 6 | 73 ± 3 |
| Ex. 9 | 8 | 1 | 5 | 7 | 2 | 7 | 101 ± 18 | 150 ± 27 | 61 ± 5 | 74 ± 3 |
| Ex. 9-2 | 10 | 3 | 3 | 6 | 2 | 6 | 102 ± 24 | 148 ± 18 | 59 ± 3 | 67 ± 2 |
| Ex. 10 | 9 | 2 | 4 | 8 | 2 | 5 | 110 ± 23 | 178 ± 30 | 60 ± 4 | 89 ± 5 |
| Ex. 10-2 | 11 | 5 | 2 | 7 | 2 | 3 | 104 ± 16 | 142 ± 21 | 52 ± 6 | 79 ± 5 |
| Ex. 11 | 10 | 3 | 4 | 8 | 1 | 4 | 107 ± 25 | 169 ± 26 | 57 ± 5 | 69 ± 2 |
| Ex. 11-2 | 13 | 7 | 2 | 6 | 0 | 2 | 102 ± 20 | 151 ± 24 | 55 ± 4 | 65 ± 4 |

13

14

As a result, it was confirmed that the compositions of Examples 1 to 11-2, which contain momordin Ic, platycodin D2, polygalacin D, asiaticoside B, bacopaside I, notoginsenoside R2, picfeltarraenin IB, pseudoginsenoside RT5, raddeanin A, vina-ginsenoside R4 or ziyuglycoside II, showed the effect of preventing hair loss and promoting hair growth. In particular, the formulations containing ethanol showed better effect of preventing hair loss and promoting hair growth. Through this, it was confirmed that the composition for preventing hair loss and promoting hair growth of the present disclosure, which contains momordin Ic, platycodin D2, polygalacin D, asiaticoside B, bacopaside I, notoginsenoside R2, picfeltarraenin IB, pseudoginsenoside RT5, raddeanin A, vina-ginsenoside R4 or ziyuglycoside II as an active ingredient, can be very usefully used for treatment of hair loss. It will be obvious to those having ordinary knowledge in the art that the formulation examples such as the hair tonic or hair lotion are only the examples of the composition for preventing hair loss or promoting hair growth of the present disclosure and the scope of the present disclosure composition is not limited to the formulations.

As other examples, a shampoo composition according to an exemplary embodiment of the present disclosure is described in Table 8 and a conditioner composition according to an exemplary embodiment of the present disclosure is described in Table 9.

TABLE 8

| Ingredients | Contents (wt %) |
|---|---|
| Active ingredient for preventing hair loss and promoting hair growth | 0.01 |
| Polyquaternium-10 | 0.5 |
| Sodium lauryl sulfate | 10 |
| Oil | 1 |
| Thickener | 5 |
| Flavorant | 0.5 |
| Sodium chloride | Adequate |
| Citric acid | Adequate |
| Water | Up to 100 wt % |

TABLE 9

| Ingredients | Contents (wt %) |
|---|---|
| Active ingredient for preventing hair loss and promoting hair growth | 0.01 |
| Stearamidopropyl diethylamine | 2 |
| Dicetyldiethylammonium chloride | 1 |
| Cetyl alcohol | 3 |
| Stearyl alcohol | 4 |
| Cyclomethicone | 5 |
| Flavorant | Adequate |
| Water | Up to 100 wt % |

What is claimed is:

1. A method of alleviating hair loss or promoting hair growth comprising: administering to a subject in need thereof a composition comprising an active ingredient selected from a group consisting of momordin Ic, platypodid D2, polygalacin D, notoginsenoside R2, picfeltarraenin IB, pseudoginsenoside RT5, raddeanin A, vina-ginsenoside R4 and ziyuglycoside II, and thereby alleviating hair loss or promoting hair growth in the subject, wherein the active ingredient is in an amount of 0.0001-0.1 wt. % based on the total weight of the composition, and wherein the composition enhances the activity of the Wnt/β-catenin signaling pathway in dermal papilla cells.

2. The method for alleviating hair loss or promoting hair growth according to claim 1, wherein the composition enhances the activity of dermal papilla cells.

3. The method for alleviating hair loss or promoting hair growth according to claim 1, wherein the composition inhibits the action of male hormones.

* * * * *